US00PP14485P29

(12) United States Plant Patent
Lyrene

(10) Patent No.: US PP14,485 P2
(45) Date of Patent: Jan. 27, 2004

(54) BLUEBERRY PLANT CALLED 'FLORIDA ROSE'

(50) Latin Name: *Vaccinium ashei*
Varietal Denomination: Florida Rose

(75) Inventor: Paul M. Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 33 days.

(21) Appl. No.: 10/327,522

(22) Filed: Dec. 24, 2002

(51) Int. Cl.[7] ..... A01H 5/00
(52) U.S. Cl. ..... Plt./157
(58) Field of Search ..... Plt./157

*Primary Examiner*—Bruce R. Campell
*Assistant Examiner*—June Hwu

(57) ABSTRACT

A new and distinct low-chill rabbiteye blueberry (*Vaccinium ashei*) cultivar. Its novelty consists of the following unique combination of features:

1. Has a low chilling requirement.
2. When grown in full sun, produces berries which, when mature, are pink to red on top and pink to white on the bottom.
3. Berries average about 1.3 g in weight and are sweet and low-acid when ripe.
4. The plant is vigorous and upright in growth habit.
5. The plant reaches 50% flowering about March 15 and 50% ripe fruit about May 25 when grown in the field in Gainesville, Fla.

4 Drawing Sheets

Latin name of the genus and species: *Vaccinium ashei* Reade.
Variety denomination: 'Florida Rose'.

BACKGROUND OF THE INVENTION

Rabbiteye blueberries are native in the southeastern United States. The normal fruit color is black or powdery blue. The first improved rabbiteye cultivars were released in the 1950s. Other cultivars have been released since then, and cultivation of rabbiteye blueberry for the commercial fresh and processed berry markets has become a significant industry in the southeastern United States, in Chile, in Australia and in New Zealand. Several hundred hectares of rabbiteye blueberries have been planted for pick-your-own markets from Florida to North Carolina and west to Texas, and thousands of plants of various rabbiteye blueberry cultivars are sold each year as home landscape and garden plants.

Rabbiteye blueberry breeding began at the University of Florida about 1950, with the goal of developing early-ripening, disease resistant plants that would produce high-quality berries when grown in areas with mild winters. Eight cultivars have been released from this program. In 1984, in a population of 100 seedlings grown from a cross-made in Florida, one seedling appeared whose mature fruit were purple, rather than black or blue, which are the normal colors for rabbiteye blueberries. This plant was subsequently used in a recurrent selection program to develop 'Florida Rose', which has a bright pink fruit color. Because of the bright, attractive color of the fruit, 'Florida Rose' has the potential to provide a novel ornamental shrub for fruit production and for landscape planting. The clone could also be used to provide unique and attractive berries for both the fresh and processed blueberry markets. Producers of canned fruit cocktails, who have hitherto avoided blueberries because dark, water-soluble pigments from the skin diffuse into the fruit mix, could use the berries of 'Florida Rose' to enhance the bright, attractive color of their fruit mixes.

The seed that gave rise to 'Florida Rose' was obtained by hand pollination in a greenhouse at the University of Florida in Gainesville in March 1994. Both the seed parent (FL94-88) and the pollen parent (FL94-81) were selections developed in the University of Florida blueberry-breeding program. Neither parent is patented and neither has been released as a cultivar. 'Florida Rose' differs from its parent FL94-88 in having a plant with higher vigor, more resistance to blueberry rust and to Phytophthora root rot, and a smaller berry. By having bright, pink fruit it differs from its parent FL94-81, which has black fruit. 'Florida Rose' differs from all other released rabbiteye blueberry cultivars because of the unusual color of its mature fruit. The original seedling of 'Florida Rose' fruited for the first time at The University of Florida Horticultural Unit in Gainesville in May 1996. Because of its attractive berry and vigorous bush, plants were propagated by softwood cuttings to establish a 10-plant field plot and a 20-plant nursery plot of potted plants. Based on the performance of these plants in subsequent seasons, the clone was selected for further propagation and naming in June 2002.

Several hundred plants of 'Florida Rose' have been asexually propagated by softwood cuttings at the University of Florida, and none of the resulting plants has shown any deviation from the original plant in berry or bush characteristics.

BRIEF SUMMARY OF THE INVENTION

'Florida Rose' has the following novel combination of characteristics that set it apart from other blueberry cultivars.

a. The ripe fruit is pink on the top side (exposed to full sunlight) and white on the bottom side (not exposed to full sunlight).
b. The berries are large (1.2 to 1.7 g) with good firmness, a small dry picking scar, a sweet flavor, small seeds, and inconspicuous grit cells.

c. The plant has a low chilling requirement, and opens both flower and leaf buds as far south as Gainesville, Fla., even after milder than normal winters.

d. Despite its low chilling requirement, the plant flowers with 'Brightwell' (unpatented), a mid to late-flowering rabbiteye blueberry that seldom suffers from spring frost in Gainesville, Fla.

e. The berry ripens early in the season, with a 50% ripe date of about May 25 in Gainesville, Fla.

f. The plant propagates readily from softwood cuttings and grows vigorously in nursery beds or pots of pine bark.

BRIEF DESCRIPTION OF THE DRAWING

The color chart used in this specification in "The Pantone Book of Color", by Leatrice Eiseman and Lawrence Herbert. 1990. Harry N. Abrams, Inc., Publishers, N.Y. Where colors in the drawings differ from the Pantone color designations in the verbal descriptions, the Pantone color designations are the more accurate.

The first drawing shows several flower clusters of 'Florida Rose' including individual flowers with calyx, corolla, and the styles extending beyond the tip of the corolla tube. The appearance of the flowers before anthesis is also shown.

The second drawing shows the leaves, stems, and ripe fruit of 'Florida Rose'.

The third drawing shows, at close distance, the ripe fruit of 'Florida Rose' and their arrangement in fruit clusters.

The fourth drawing shows harvested berries of 'Florida Rose' showing the variation in colors between the side of the berry that was exposed to full sunlight during development and the side that was partially shaded.

DETAILED BOTANICAL DESCRIPTION

Market Class. 'Florida Rose' produces rabbiteye blueberries that are suitable for both the fresh and processed blueberry markets.

Bush: Plant characteristics were measured on 3-year-old plants planted into unamended soil in a field in Gainesville, Fla., provided with overhead irrigation, and fertilized according to commercial practices.

*Plant height.*—1.2 m.

*Canopy diameter measured at widest part of bush.*—1.4 m.

*Plant vigor.*—Medium to high. Equal to 'Climax' (unpatented).

*Growth habit.*—Between spreading and upright.

*Flower bud density (number) along flowering twigs in January.*—High.

*Twigginess.*—Medium.

Trunk:

*Suckering tendency.*—Medium to high. Three-year-old plants have 10 main sprouts from the base.

*Surface texture of 6-month-old stems observed September 20.*—Smooth.

*Suface texture of strong, 1-year-old shoots observed September 20.*—Changing from smooth to rough. Vertical cracks appear in the smooth stems. A rough corky growth fills these cracks. By the time the canes are 3 years old, the rough, corky material has exfoliated and the stems are again essentially smooth. This is a normal pattern of stem thickening in rabbiteye blueberry.

*Surface texture of 3-year-old canes.*—Smooth.

*Color of 6-month-old smooth stems viewed September 20.*—'Sweet Pea', Pantone 15-0531.

*Color of 2-year-old rough, corky canes.*—'Café Creme', Pantone 16-1220 (a shade of brown).

*Color of 3-year-old smooth canes after exfoliation.*—'Crystal Gray', Pantone 13-3801.

*Internode length on strong upright twigs measured September 20.*—17 mm.

Leaves:

*Leaf length for fully expanded leaves including the petiole.*—58 mm.

*Leaf length at widest point.*—25 mm.

*Leaf shape.*—Oval. Leaf apex mucronate, terminating in a narrow dew tip about 0.8 mm long.

*Leaf margin.*—Finely serrate.

*Color of upper surface of leaves.*—'Tarragon', Pantone 15-0326.

*Color of lower surface of leaves.*—'Nile', Pantone 14-0223.

*Pubescence on upper surface of leaves.*—Short, white pubescence on basal part of midrib visible at 30× magnification; otherwise glabrous.

*Pubescence on lower surface of leaves.*—Gland-tipped hairs scattered over lower surface.

*Pubescence on leaf margins.*—Both sessile glands and short, gland-tipped hairs along the leaf margins. The sessile glands are most numerous on the lower (petiole) half of the leaf margin and the glandular hairs are most numerous on the apical half of the leaf margin.

Flowers:

*Flower arrangement.*—Flowers arranged alternately along a short, leafless, deciduous branch.

*Fragrance.*—None.

*Pedicel length at time of anthesis.*—Mean=6.1 mm.

*Peduncle length at time of anthesis.*—Mean=6.2 mm.

*Petals.*—Fused into a corolla tube with 5 lobes.

*Pollen staining.*—Approximately 98% of the grains stain with acetocarmine dye, indicating that a high percentage of the pollen grains are normal, plump, and potentially viable.

*Pollen abundance.*—Dried flowers shed pollen abundantly.

*Pollen color.*—'Reed yellow', Pantone 13-0915.

*Flower type.*—Perfect, ovary inferior, petals fused into a corolla tube, the 10 stamens inserted at the base of the corolla tube.

*Flower length, pedicel attachment point to corolla tip.*—Mean=12.1 mm.

*Style length, top of ovary to stigma tip.*—Mean=10.1 mm.

*Calyx diameter at anthesis, tip of opposite lobe.*—Mean=3.5 mm.

*Diameter of corolla tube at widest point.*—Mean=5.7 mm.

*Corolla aperture diameter.*—Mean=2.3 mm.

*Corolla surface texture.*—Smooth.

*Flower shape.*—Cylindrical.

*Corolla color at anthesis.*—'Pearl', Pantone 12-1304, (a light pink) on plants flowering outside when overnight minimum temperatures fall below 7° C. during flowering. On plants that flower in a warm greenhouse, the flowers are pure white.

*Calyx color at anthesis.*—'Green tint', Pantone 13-6106.

*Flowering period.*—Date of 50% open flower averages about March 15 in Gainesville, Fla., which is similar to the rabbiteye blueberry cultivar 'Brightwell' (unpatented) and 10 days after 'Climax' (unpatented).

*Flower cluster(tight, medium, or open).*—Medium to open.

*Number of flowers per cluster.*—Mean 6.9.

*Self fruitfulness.*—Very low. Zero ripe berries were harvested from 80 flowers self-pollinated in a greenhouse. 'Florida Rose' is cross compatible with all rabbiteye blueberry cultivars, such as 'Powderblue' (unpatented) and 'Brightwell' (unpatented) that flower during the same period.

*Location of tip of style relative to lip of corolla.*—Stigma tip extends 1 mm beyond corolla tube.

Berry:

*Mean date of 50% fruit ripe.*—About May 25 in Gainesville, Fla. This is about equal to the rabbiteye blueberry cultivar 'Climax' (unpatented), 10 days before the rabbiteye blueberry cultivar 'Brightwell' (unpatented), and 15 days before the rabbiteye blueberry cultivar 'Powderblue' (unpatented).

*Diameter of calyx aperture on mature berry.*—Mean = 4.4 mm.

*Calyx lobes on mature berry size and shape.*—Calyx lobes small, resulting in a calyx aperture that is nearly round. Calyx lobes appressed to the surface of the berry.

*Berry cluster (tight, medium, or open).*—Medium.

*Pedicel length on ripe berry.*—Mean=6.5 mm.

*Peduncle length at the time berries are ripe.*—Mean= 5.1 mm.

*Number of ripe berries per cluster.*—Mean=4.3.

*Mean berry weight on well-pruned plants.*—1.3 g.

*Mean berry height.*—11.7 mm.

*Mean berry width.* —12.4 mm.

*Berry color (ripe) on plant.*—'Sunkist Coral', Pantone 17-1736 on parts exposed to direct sunlight during ripening; 'Silver Peony', Pantone 12-1206 on parts not exposed to direct sunlight (such as the bottom sides of the berries) during ripening.

*Berry color after harvest and moderate handling.*—'Sunkist Coral', Pantone 17-1736 on the parts exposed to direct sunlight during ripening; 'Silver Peony', Pantone 12-1206, on parts not exposed to direct sunlight during ripening.

*Berry skin color after polishing.*—'Calypso Coral', Pantone 17-1744, on parts exposed to direct sunlight during ripening; 'Silver Peony', Pantone 12-1206, on parts not exposed to direct sunlight during ripening.

*Internal flesh color of ripe berry.*—'Sheer Pink', Pantone 12-1106.

*Berry skin color when grown in a greenhouse with light intensity reduced to about 25% of full sunlight.*—'White swan', Pantone 12-0000.

*Berry surface wax.*—Sparse to medium in abundance, medium in persistence in the face of berry handling.

*Berry pedicel scar.*—Small and dry.

*Berry firmness.*—High.

*Berry flavor.*—Sweet with low acidity.

*Berry texture.*—Smooth; seeds small and grit (stone cells) not noticable.

*Color of dried seed.*—'Biscuit', Pantone 16-1336.

*Weight of well-developed, dried seed.*—0.59 mg per seed.

*Length of the largest, fully-developed seed.*—2.3 mm.

*Width of the largest, fully-developed seed.*—1,5 mm.

Physiological characteristics:

*Chilling requirement.*—About 300 hours per winter of temperatures below 7° C. Despite the low chilling requirement, the clone does not flower extremely early, probably because it has a medium to high heat requirement.

*Cold hardiness.*—Open flowers and fruit are hardy to −3 ° C. Plants in full winter dormancy are hardy to −15° C.

*Productivity.*—Three-year-old plants produce about 1.5 kg per bush. Six-year-old plants produce about 3 kg per bush.

Diseasess, insects, mites:

*Phytophthora root rot.*—Medium resistance. Slightly more susceptible than 'Climax' (unpatented).

*Stem blight (Botryosphaeria dothidia).*—Medium resistance.

*Stem canker (Botryosphaeria corticis).*—Resistant.

*Fungal and bacterial leaf spots.*—Resistance about average for rabbiteye blueberry. Fungicide sprays may be needed during summer to maximize yields in commercial plantings.

*Blueberry bud mites.*—Resistant.

*Overall survival in the field.*—Medium. Slightly more plant loss than for 'Climax' (unpatented).

Ease of propagation: 'Florida Rose' is easy to propagate from softwood cuttings and grows vigorously in nursery pots.

I claim:

1. A new and distinct rabbiteye blueberry plant, substantially as illustrated and described, characterized by having a vigorous bush and a berry that is large, sweet, and pink to white in color when fully ripe.

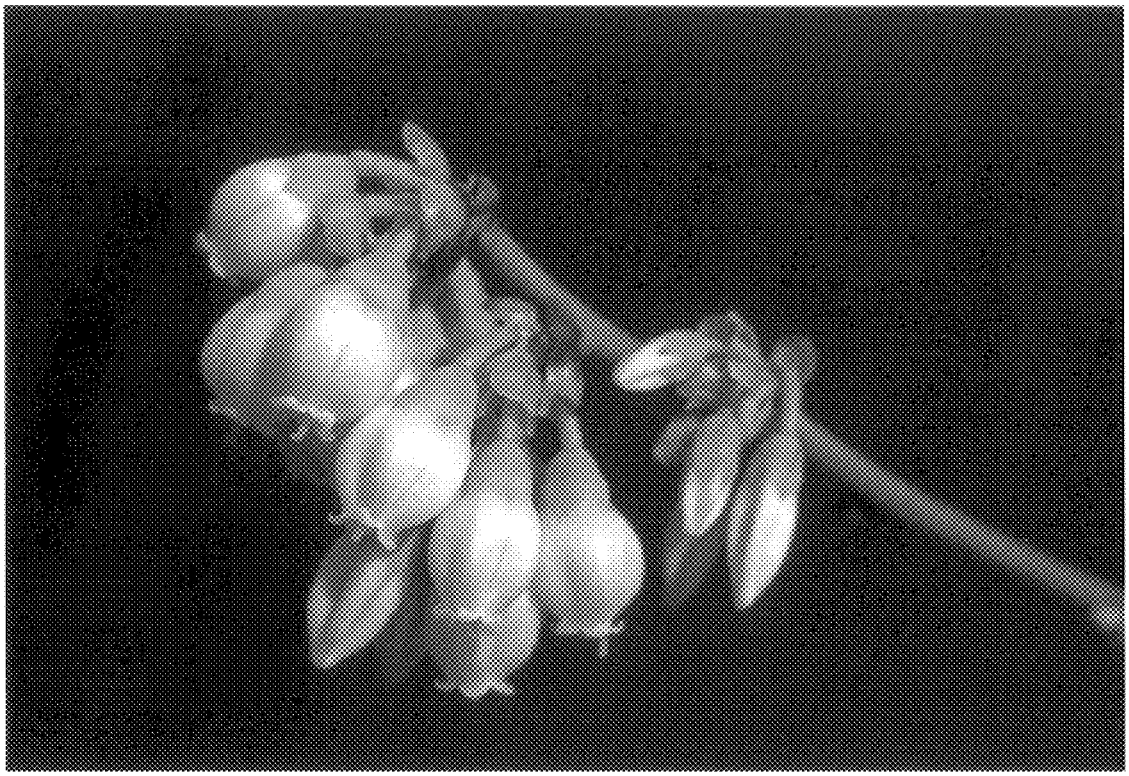

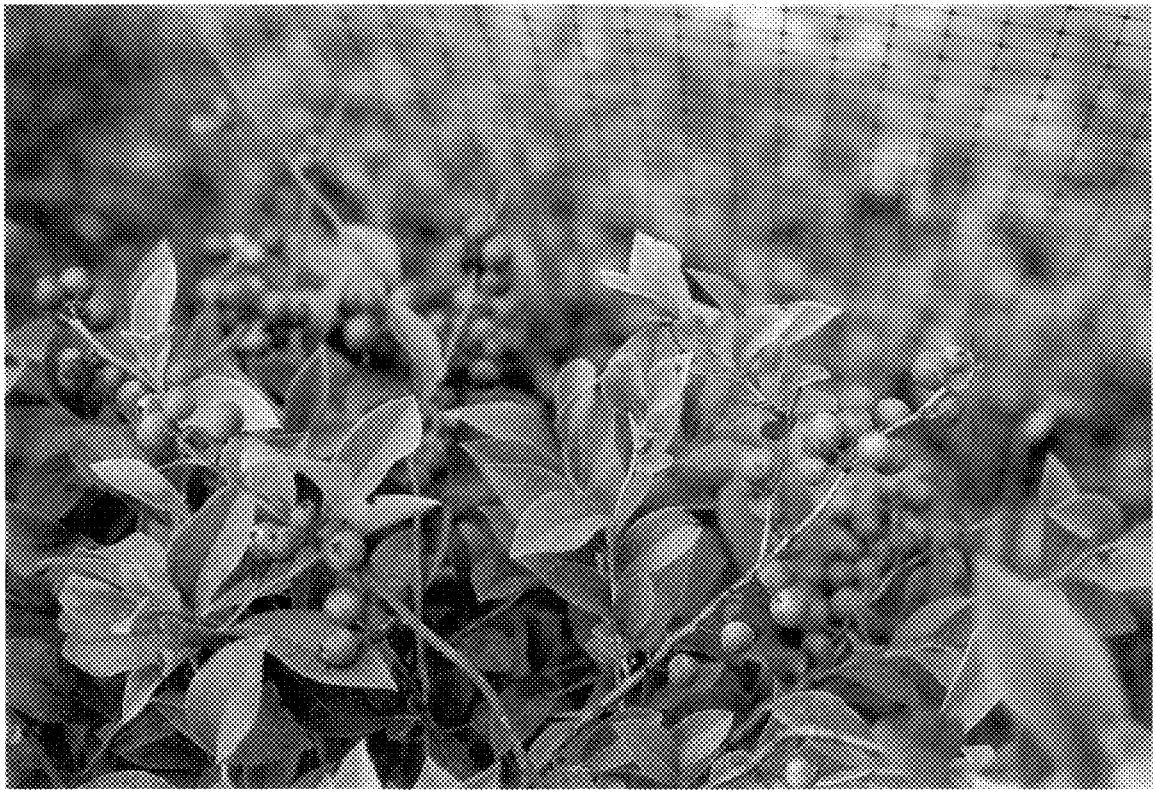

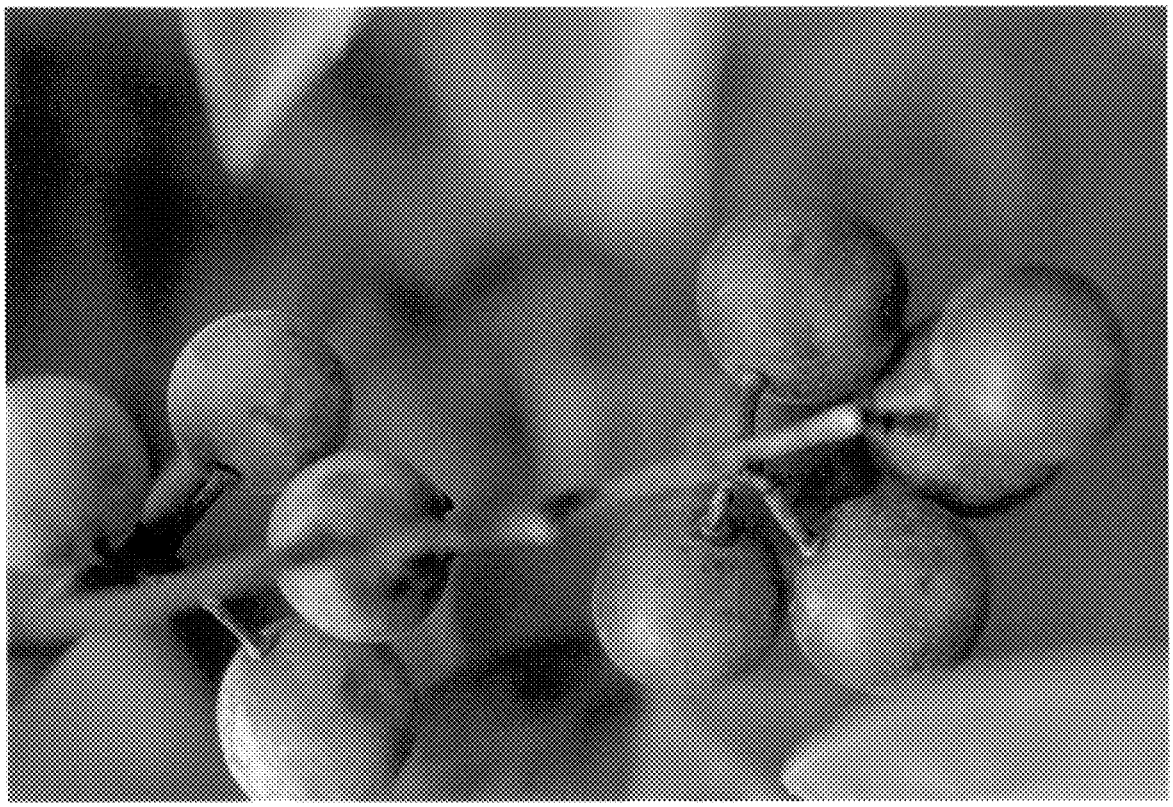

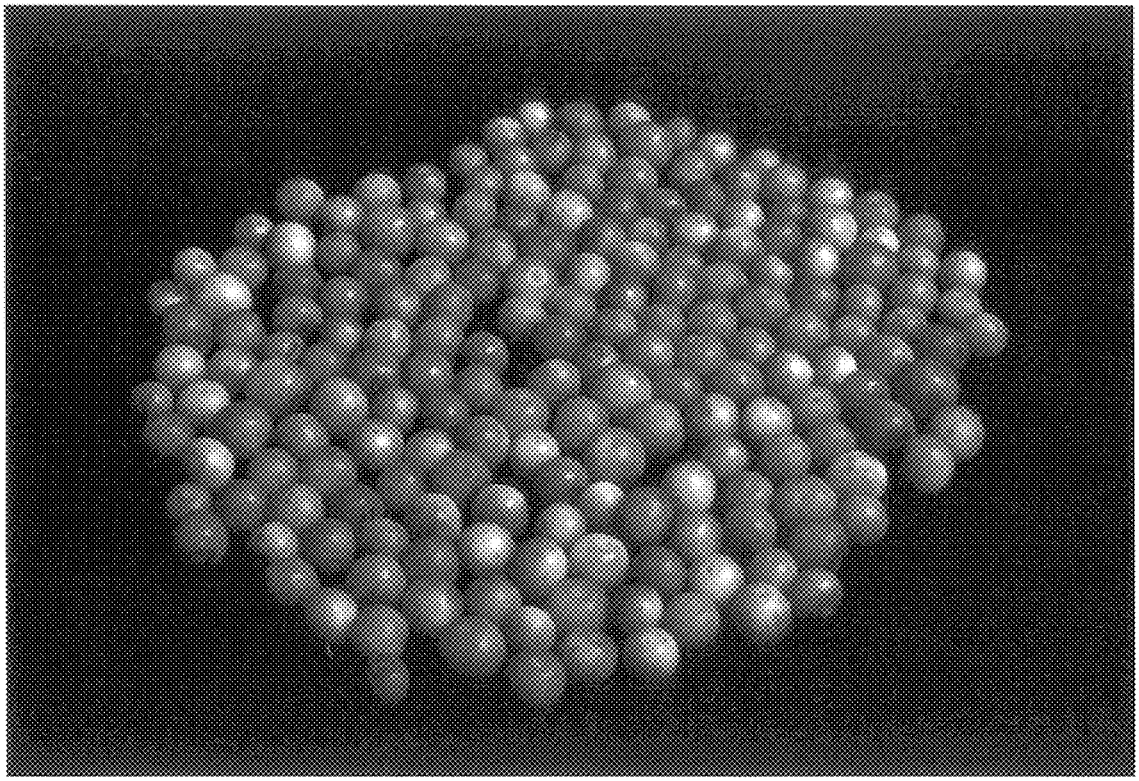

* * * * *